United States Patent [19]

Puritch et al.

[11] Patent Number: 5,047,424

[45] Date of Patent: * Sep. 10, 1991

[54] ENVIRONMENTALLY SAFE INSECTICIDE

[75] Inventors: George S. Puritch, Saanichton; Gregory S. Salloum, Victoria, both of Canada

[73] Assignee: Safer, Inc., Newton, Mass.

[*] Notice: The portion of the term of this patent subsequent to Feb. 27, 2007 has been disclaimed.

[21] Appl. No.: 252,786

[22] Filed: Oct. 3, 1988

[51] Int. Cl.$^5$ .................... A01N 53/00; A61K 31/215
[52] U.S. Cl. ...................................... 514/521; 514/65; 514/69; 514/531; 514/560
[58] Field of Search .................... 514/531, 65, 66, 67, 514/174; 523/523

[56] References Cited

U.S. PATENT DOCUMENTS

| | | | |
|---|---|---|---|
| 2,374,918 | 5/1945 | Brown et al. | 514/560 |
| 4,469,675 | 9/1984 | Curtis et al. | 514/524 |
| 4,617,318 | 10/1986 | Morel | 514/520 |
| 4,668,511 | 5/1987 | Aspirot et al. | 424/93 |
| 4,774,234 | 9/1988 | Puritch et al. | 514/560 |
| 4,791,127 | 12/1988 | Kato et al. | 514/369 |

FOREIGN PATENT DOCUMENTS

| | | |
|---|---|---|
| 0001809 | 10/1978 | European Pat. Off. |
| 61-24585 | 2/1986 | Japan |
| 2058569 | 4/1981 | United Kingdom |
| 2095109 | 9/1982 | United Kingdom |
| 2113092 | 8/1983 | United Kingdom |

OTHER PUBLICATIONS

Product Bulletin "Mavrick Aquaflow—Greenhouse Use" May, 1988.
"Sweet Potato Whitefly: A Tiny Pest with a Big Appetite for Greenhouse Ornamentals" May, 1988 Issue of *Sandoz Spotlight*.
Pyrethrum and Soap, A Chemically Incompatible Mixture, Roark, 23 Journal of Economic Entomology 460.
The Effect of Soap on the Toxicity of a Pyrethrum Product Known as "Red Arrow", Badertscher, 24 Journal of Economic Entomology 268.
Composition of Pyrethrum Extract and Analysis of Pyrethrins, Head, *Insecticidal Value of Pyrethrum Soaps*, Cory and Eaton, Bulletin No. 308, (1929) The Maryland Agricultural Experiment Station.

*Primary Examiner*—Thurman K. Page
*Assistant Examiner*—Peter F. Kulkosky
*Attorney, Agent, or Firm*—Saliwanchik & Saliwanchik

[57] ABSTRACT

An environmetally safe, broad spectrum insecticidal composition is disclosed. The composition combines a mixture of monocarboxylic acids (such as oleic and linoleic) and their alkali metal salts, and a pyrethroid compound. In a concentrated form of the composition, the monocarboxylic acid mixture comprises about 50 percent by weight monocarboxylic acids and their salts, at least 70 percent of which comprise oleic acid and at least 6 percent comprise linoleic acid. The pyrethroid compound is present in the concentrate at about 0.2 to 2.0 percent by weight.

15 Claims, No Drawings

ENVIRONMENTALLY SAFE INSECTICIDE

BACKGROUND OF THE INVENTION

This invention relates to an environmentally safe insecticidal composition. More particularly, the invention features a specific insecticide formulation combining certain fatty acid soaps and pyrethroids.

The use of insecticides has greatly enhanced agricultural productivity, but it has become apparent that there are limits to the amount of petrochemical-based materials that safely can be absorbed into the environment. Catastrophic, unanticipated, relatively long term effects experienced with materials such as DDT have increased awareness of the potentially dangerous environmental impact of widespread use of synthetics, contributed to the creation of regulatory agencies charged with protecting the environment, and promoted the development of potent, but apparently less dangerous insecticidal materials made from petrochemicals. These new insecticides are nevertheless far from ideal from the point of view of environmental safety, and sometimes collect in food and fresh water resources.

Recently, natural insecticidal materials such as bacterial preparations lethal to insects have been available commercially. However, the potential of non-bacterial, natural materials having insecticidal properties has largely been ignored, presumably because of the higher cost and lower insecticidal activity of such known natural substances.

Salts of fatty acids, primarily sodium or potassium fatty acid soaps, recently have been used commercially as insecticides. Compositions having excellent insecticidal properties which exploit these salts are available commercially under the trademark SAFER INSECTICIDAL SOAP. This product accordingly constitutes an exception to the trend noted above. These fatty acid soaps are naturally occurring materials having no known long term environmental effects. They are very effective against soft bodied insects such as aphids and whiteflies, but less effective against other types of insects.

Pyrethrum was used commercially many years ago as an insecticide, primarily in the form of "oleoresin of pyrethrum". Oleoresin of pyrethrum is an archaic pharmaceutical term for an ether extract of the cinerariaefolium variety of chrysanthemum. It contains volatile oils and components having insecticidal properties, called pyrethrins and cinerins. These materials are known to be toxic to insects, but essentially non-toxic to mammals. Pyrethrins also lack persistence in the environment, and are characterized by negligible biological magnification in the food chain.

One major problem with the use of these pyrethrins as insecticides is their high cost per unit dose. Attempts to extend the efficacy of the pyrethrins to provide economic feasibility have not been commercially successful. An example of such a composition comprising a mixture of saponified organic acids, i.e., salts of coconut oil, and pyrethrins was once sold commercially under the trademark Red Arrow. However, these compounds were still not economically feasible because of their high pyrethrin content (about 40% by weight), and because the coconut oil soaps contributed little to their insecticidal efficacy. In fact, most commercially available fatty acid soap compositions contain an excess of alkali which is believed to promote hydrolysis and inactivation of pyrethrins. Pyrethrin-based insecticides also degrade rapidly in the presence of sunlight and during storage.

Other materials which have been used to extend the efficacy of pyrethrins are toxic not only to insects but also to a variety of plants and animals. One material often suggested for use with pyrethrins is piperonyl butoxide. While this type of composition can produce a very potent insecticide, high doses can cause nausea in many animals including man, and the compositions are significantly phytotoxic. Other combinations of insecticides and pyrethrins have either presented similar toxicity concerns or loss of effectiveness due to inactivation of the pyrethrins.

U.S. patent application Ser. No. 148,961 discloses an insecticidal formulation which combines pyrethrins and salts of fatty acids. Although this composition is environmentally safe and demonstrates improved insecticidal properties, it is still relatively expensive and may be susceptible to degradation during storage or use because of the presence of pyrethrins.

Accordingly, it would be advantageous to provide an environmentally safe and effective insecticidal composition which has improved storage properties and is not particularly prone to degradation upon exposure to sunlight.

It is thus an object of this invention to provide an insecticide formulation comprising natural, biodegradeable materials which are relatively inexpensive, non-toxic to a wide variety of plants and animals, and effective against a broad spectrum of insect life. Another object is to provide a specific, environmentally safe insecticidal formulation which has a commercially acceptable shelf life, low, acceptable phytotoxicity, and relatively low cost.

These and other objects and features of the invention will be apparent from the description and the claims which follow.

SUMMARY OF THE INVENTION

The present invention features an aqueous insecticidal solution comprising a combination of active, readily biodegradeable insecticidal materials. This combination of active insecticidal materials has been observed to enhance the effectiveness of the individual insecticidal materials. The insecticidal solution is effective in protecting a variety of plants against a variety of insects and related pests. Moreover, the insecticide is economical to use and substantially non-toxic to plants and animals.

The insecticidal formulation comprises a first insecticidal component comprising a mixture of carboxylic acids and the alkali metal salts of the acids. The carboxylic acids of this mixture comprise oleic acid, and its alkali metal salts, as a major component, and linoleic acid, and its alkali metal salts, as a minor component. Other carboxylic acids, and their salts, having less than 21 carbon atoms may also be present in the mixture. A second insecticidal component of the insecticidal formulation comprises a pyrethroid compound. Although virtually any insecticidally active pyrethroid compound may be used with the invention, the currently preferred pyrethroids include cypermethrin, fenvalerate, fluvalinate and permethrin. A solvent for the pyrethroid, such as an alcohol having between 2 and 6 carbon atoms (e.g. ethanol or isopropanol), may be included in the insecticidal formulation to help solubilize the fatty acid salts at higher concentrations (e.g., greater than 20%).

A concentrated formulation may be diluted from between 25:1 to 500:1 with water to yield a ready-to-use formulation. The ready-to-use formulation is effective on application to a plant at a dilution in water such that the applied solution contains at least about 0.05–2.0 percent by weight of the monocarboxylic acid mixture and at least 0.001 percent of an insecticidally active pyrethroid compound.

This insecticidal formulation provides protection against plant damage from infestation from insect species from at least the orders Homoptera; Coleoptera; Dermaptera; Hemiptera; and Lepidoptera; and from crustacea species from the order Isopoda. More specifically, application of the solutions is effective against species from the families *Homoptera aphididae; Homoptera aleyrodidae; Homoptera coccidae; Homoptera psyllidae; Coleoptera chrysomelidae; Coleoptera tenebrionidae; Lepidoptera arctiidae; Lepidoptera lasiocampidae; Lepidoptera tortricidae; Lepidoptera pieridae;* and *Lepidoptera noctuidae.* These orders and families include essentially all northern hemisphere insects which damage ornamental plants, trees, and vegetable crops. The insecticidal solutions also are effective in the control of mosquitoes, fleas, lice, and ticks, and accordingly may be used, for example, to protect pets and their resting places in the home.

The insecticide of the invention is useful in protecting apples, avocados, grapefruits, lemons, oranges, tangerines, peaches, nectarines, apricots, pears, almonds, pecans, walnuts, kiwi fruit, blackberries, logan berries, raspberries, strawberries, and grapes, against insects including Japanese beetles, flea beetles, weevil adults, caterpillars, aphids, leaf hoppers, psyllids, scale crawlers, and sawfly larvae. In addition to commercial or vegetable garden protection, the insecticide of the invention can be used to protect lawns, turf grass, ornamental trees and shrubs, flowers, and house plants against a variety of insects. For example, the insecticide protects lawns against chinch bugs, lawn moth, sod webworm and army ants, and ornamental trees and shrubs against aphids, beetles, caterpillars, lace bugs, box elder bug, treehoppers, psyllids, sawflies, scales, and woolly aphids. Essentially complete insect protection is provided for ornamental trees and shrubs including azaleas, camellias, cacti, dogwood, rhododendrons, evergreens, and broad-leafed shade trees. The insecticide of the invention has been shown to provide effective protection for flowers including asters, carnations, chrysanthemums, geraniums, marigolds, petunias, and roses against attack by aphids, flea beetles, Japanese beetles, caterpillars, and whitefly.

DETAILED DESCRIPTION OF THE INVENTION

As noted previously, the insecticidal formulation of this invention combines two insecticidally active materials (fatty acid soaps and pyrethroids) to obtain insecticidal effectiveness which is superior to the effectiveness of either of the two components alone. Generally, it is possible to combine the insecticidal components of the invention in varying amounts to form an aqueous solution. However, as pyrethroid compounds are more insecticidally potent than the fatty acid soaps, the pyrethroid component generally may be present in smaller amounts.

The insecticide of the invention is preferably prepared as a concentrate and is subsequently diluted for use to a ready-to-use form. A preferred formulation, in concentrate form, comprises (1) approximately 50 percent by weight of an aqueous solution of carboxylic acids and the alkali metal, preferably potassium, salts thereof; (2) approximately 0.2 to 2.0 percent by weight of a pyrethroid compound; (3) about 30 percent by weight of an alcohol having between 2 and 6 carbon atoms; and (4) water. The concentrate may be diluted from between 25:1 to 500:1, and preferably from about 50:1 to about 100:1, with water to yield a ready-to-use formulation comprising about 1.0 percent by weight carboxylic acids and at least 0.001 percent by weight of a pyrethroid compound. Preferably, the pyrethroid compound is present from about 0.002 percent by weight to 0.04 percent by weight.

In a currently preferred embodiment the carboxylic acid mixture comprises, in an aqueous solution, approximately 10 to 50 percent by weight, and most preferably about 49 percent, of a mixture of the alkali metal salts of fatty acids and unneutralized fatty acids.

A suitable carboxylic acid solution is available commercially from Safer, Inc. of Wellesley, Mass. under the trademark "Safer Insecticidal Soap". The composition of this product varies slightly from batch to batch, but its carboxylic acid component always includes at least about 70% salt (or acid) form of oleic acid, and at least about 6% salt (or acid) form of linoleic acid. The remainder of the solutes comprise other fatty acids or salts having between 12 and 20 carbon atoms. The soap component is present in the concentrate at levels in the range of 10 to 50, preferably about 49, percent by weight.

The pyrethroid component comprises about 0.2–2.0 percent, by weight of the concentrate. Upon dilution to a ready-to-use formulation the pyrethroid component is present at between about 0.001 to 0.04, and preferably between about 0.009 and 0.025 percent by weight. The pyrethroid compounds useful with this invention are esters which have been developed in response to the high cost and rapid breakdown of natural pyrethrins. These synthetic compounds have the insecticidal activity associated with that of the naturally occurring pyrethrins, without their high cost, erratic supply or low environmental stability.

Virtually any known pyrethroid compound having insecticidal activity is useful with the practice of this invention. Such useful pyrethroids include, but are not limited to alfoxylate, cyfluthrin, cyhalothrin, cypermethrin, cyphenothrin, deltamethrin, esfenvalerate, fenfluthrin, fenopropathrin, fenpyrithrin, fenvalerate, fluorocythrin, furamethrin, fluvalinate, permethrin, phencyclate, phenothrin; tetrallethrin, tralocythrin and tralomethrin. Currently, the most preferred pyrethroids are cypermethrin, fenvalerate, fluvalinate and permethrin.

Preferred cypermethrin compounds are available from BASF (India) under the trademark "Basathrin"; from FMC, Agri. Chem. Group under the trademarks "Ammo", "Arrivo", and "Cynoff"; from ICI Americas, Inc., Agri. Chem. Div. under the trademark "Cymbush"; from IGI Agrochemicals (U.K.) under the trademarks "Cymbush", "Kafil Super" and "Cymperator"; from Mitchell Cotts Chem. Ltd. (U.K.) under the trademark "Cyperkill"; from Shell Int'l Chem. Co., Ltd. (London) under the trademarks "Barricade", "Flectron", "Folcord" and "Ripcord"; and from United Phosphorous, Ltd. (India) under the trademarks "Ustaad 10EC" and "Cyroxy 25EC".

Fenvalerate compounds are available from E. I. du Pont de Nemours & Co., Inc. Agri. Products Dept. under the trademark "Pydrin"; from Fermenta Animal Health under the trademark "Ectrin"; from Rallis India Ltd. under the trademark "Sumicidin"; from Shell Intl. Chem. Co., Ltd. (London) under the trademark "Belmark"; from Sumitomo Chem. Co., Ltd. (Japan) under the trademark "Sumicidin"; and from United Phosphorus Ltd. (India) under the trademark "Fenkill".

Fluvalinate compounds are available from Sandoz Crop Protection Corp. under the trademark "Mavrik".

Permethrin compounds are available from FMC Agri. Chem. Group under the trademarks "Cellutec", "Dragnet", "Pounce" and "Pounce Peach"; from ICI Americas Inc., Agri. Chem. Div. under the trademarks "Ambush" and "Torpedo"; from ICI Agrochemicals (U.K.) under the trademarks "Ambush", "Dragon", "Imperator", "Kafil" and "Perthrine"; from Mitchell Cotts Chem. Ltd. (U.K.) under the trademark "Permasect"; from Penick-Bio UCLAF Corp. under the trademark "Pramex"; from Shell Int'l Chem. Co., Ltd. (London) under the trademarks "Outflank" and "Talcord"; from Sumitomo Chem. Co., Ltd. (Japan) under the trademark "Eksmin"; from Wellcome Foundation Ltd. (U.K.) under the trademarks "Coopex" and "Qamlin".

The concentrate may also include an alcohol having between 2 and 6 carbon atoms, which acts to dissolve the soap in the concentrate if the soap concentration exceeds about 20 percent. Preferred alcohols include ethanol and isopropanol, present at approximately 30 percent by weight. The balance of the concentrated formulation consists of water.

The composition is manufactured by mixing together a solution of salts of fatty acids, water and alcohol, which acts as a carrier and solvent for the pyrethroid.

A currently preferred embodiment of the concentrated formulation is made by combining and gently agitating the components of the mixture. An insecticidal solution utilizing fenvalerate as the pyrethroid is prepared by combining approximately 200 parts of potassium fatty acid soaps as previously described, 7 parts fenvalerate, 73 parts water, and 120 parts ethanol. This formulation is diluted 50:1 to 100:1 with water before application.

An insecticidal solution utilizing permethrin as the pyrethroid compound is prepared in the same way, utilizing 200 parts potassium fatty acid salts as previously described, 8 parts permethrin, 72 parts water and 120 parts ethanol. This formulation is likewise diluted 50:1 to 100:1 with water before application.

A concentrated insecticidal formulation having cypermethrin as the pyrethroid is prepared in the same way as the fluvalinate-containing formulation. In this formulation, however, 200 parts potassium fatty acids salts as previously described, 4 parts cypermethrin, 76 parts water and 120 parts ethanol are combined. This formulation is diluted 50:1 to 100:1 with water before application.

An insecticidal solution utilizing fluvalinate as the pyrethroid compound is prepared in the same way, utilizing 200 parts potassium fatty acid salts as previously described, 8 parts fluvalinate, 72 parts water and 120 parts ethanol. This concentrated formulation is diluted 50:1 to 100:1 with water before application.

Insecticidal products having the above formulations exhibit a combination of insecticidal activity, spectrum response, low vertebrate and phytotoxicity, and ready biodegradeability unavailable in any composition known to applicants. Furthermore, the storage and environmental stability of both the ready-to-use and the concentrate are improved, relative to the combination of soap and the natural pyrethrin.

The following example illustrates the efficacy and synergy of the insecticidal composition of the invention.

EXAMPLE

In this Example, a comparison of kill effectiveness was made between a fatty acid based insecticide (Safer Insecticidal Soap) alone, the pyrethroid extract alone, and an insecticide comprising a combination of the fatty acid mixture and various pyrethroids, formulated in accordance with the ratio disclosed herein. The experimental procedure involved applying the same amount of the sample to potato plants and measuring mortality percentages of the Colorado potato beetle. Table A shows the results of this experiment. As is obvious from the Table, the insecticidal formulation of the present invention does not show purely additive insecticidal properties with respect to this particular insect pest, but rather an unexpected, synergistic kill ratio.

TABLE A

| | Safer Insecticidal Soap (Conc.) | | |
|---|---|---|---|
| | 0% | 0.75% | 1.0% |
| distilled $H_2O$ | 3.1 | 0 | 12.5 |
| 0.017% fenvalerate | 25.0 | 56.7 | 48.7 |
| 0.021% permethrin | 13.6 | 20.0 | 15.9 |
| 0.009% cypermethrin | 42.9 | 90.0 | 90.0 |

What is claimed is:

1. An environmentally safe insecticidal composition, consisting essentially of:
   a solution of alkali metal salts of monocarboxylic acids, the solution comprising a predominant amount of the alkali metal salts of oleic acid and a lesser amount of the alkali metal salts of linoleic acid;
   a solvent for said pyrethroid compound comprising a low molecular weight alcohol; and
   a pyrethroid compound,
   wherein the ratio of the solution of monocarboxylic acid salts to the pyrethroid compound is at least about 2:1.

2. The composition of claim 1 wherein said low molecular weight alcohol is an alcohol having between 2 and 6 carbon atoms.

3. The composition of claim 2 wherein the solution of monocarboxylic acids comprises approximately 50 percent by weight of a mixture of alkali metal salts of monocarboxylic acids, the mixture comprising at least 70 percent by weight of the salts of oleic acid and at least 6 percent of the salts of linoleic acid.

4. The composition of claim 3 wherein the pyrethroid compound is selected from the group consisting essentially of cypermethrin, fenvalerate, fluvalinate and permethrin.

5. The composition of claim 2 wherein said alcohol solvent is ethanol.

6. The composition of claim 2 wherein said alcohol solvent is isopropanol.

7. The solution of claim 4 wherein the alkali metal salt is a potassium salt.

8. The composition of claim 7 wherein said insecticidal composition is effective against species from the families *Homoptera aphididae; Homoptera aleyrodidae;*

*Homoptera coccidae; Homoptera psyllidae; Coleoptera chrysomelidae; Coleoptera tenebrionidae; Lepidoptera arctiidae; Lepidoptera lasiocampidae; Lepidoptera tortricidae; Lepidoptera pieridae;* and *Lepidoptera noctuidae.*

9. The insecticidal composition of claim 8 comprising a concentrated formulation having the following components in the following percentages by weight:
   approximately 50 percent of a solution of alkali metal salts of monocarboxylic acids;
   from 0.2–2.0 percent of a pyrethroid compound;
   approximately 0 to 30 percent of ethanol; and
   approximately 20 to 50 percent water.

10. The composition of claim 9 wherein said concentrated formulation may be diluted from 25:1 to 500:1 with water to obtain a ready-to-use formulation.

11. The composition of claim 10 wherein said ready-to-use formulation comprises an aqeous solution having the following components in the following percentages by weight:
   from 0.05 to 2.0 percent of a mixture of alkali metal salts of monocarboxylic acids;
   from 0.002 to 0.04 percent of a pyrethroid compound; and
   0. to 0.35 percent of ethanol.

12. The composition of claim 11 wherein the pyrethroid compound is cypermethrin, and is present in the ready-to-use formulation at a concentration of 0.009 percent.

13. The composition of claim 11 wherein the pyrethroid compound is fenvalerate, and is present in the ready-to-use formulation at a concentration of 0.017 percent.

14. The composition of claim 11 wherein the pyrethroid compound is fluvalinate, and is present in the ready-to-use formulation at a concentration of 0.01 percent.

15. The composition of claim 11 wherein the pyrethroid compound is permethrin, and is present in the ready-to-use formulation at a concentration of 0.021 percent.

* * * * *

UNITED STATES PATENT AND TRADEMARK OFFICE
CERTIFICATE OF CORRECTION

PATENT NO. : 5,047,424

DATED : Sept. 10, 1991

INVENTOR(S) : George S. Puritch and Gregory S. Salloum

It is certified that error appears in the above-identified patent and that said Letters Patent is hereby corrected as shown below:

On Title Page, item [57]
Abstract     line 1:         "environmetally" should read --environmentally--

Signed and Sealed this

Ninth Day of March, 1993

*Attest:*

STEPHEN G. KUNIN

*Attesting Officer*                    Acting Commissioner of Patents and Trademarks